United States Patent [19]

Doria et al.

[11] Patent Number: 4,670,457

[45] Date of Patent: Jun. 2, 1987

[54] 2H-BENZOFURAN-3-ONE-DERIVATIVES AND PROCESS FOR THEIR PREPARATION

[75] Inventors: Gianfederico Doria, Milan; Ciriaco Romeo, Serino; Maria L. Corno, Milan, all of Italy

[73] Assignee: Farmitalia Carlo Erba, S.p.A., Milan, Italy

[21] Appl. No.: 58,736

[22] Filed: Jul. 19, 1979

Related U.S. Application Data

[63] Continuation of Ser. No. 2,380, Jan. 10, 1979, abandoned.

[30] Foreign Application Priority Data

Jan. 31, 1978 [IT] Italy .............................. 19806 A/78

[51] Int. Cl.[4] .......................................... C07D 307/83
[52] U.S. Cl. .................................... 514/470; 514/191; 514/320; 514/444; 514/826; 546/206; 549/60; 549/466

[58] Field of Search ....................... 514/470, 826, 382; 549/466, 191, 320; 546/206

[56] References Cited

U.S. PATENT DOCUMENTS

| | | | |
|---|---|---|---|
| 3,716,531 | 2/1973 | Albrecht et al. | 260/240 A |
| 4,067,993 | 1/1978 | Scherren | 424/285 |
| 4,115,567 | 9/1978 | Doria et al. | 424/250 |
| 4,143,145 | 3/1979 | Doria et al. | 424/263 |
| 4,259,340 | 3/1981 | Baker et al. | 424/269 |

OTHER PUBLICATIONS

Marathey J. Org Chem. 20 (1955) pp. 563–571.
Schenck et al. Tet. Letters #19 (1968) pp. 2379–2381.

*Primary Examiner*—Arthur P. Demers
*Attorney, Agent, or Firm*—Murray and Whisenhunt

[57] ABSTRACT

2H-Benzofuran-3-one derivatives, process for their preparation and pharmaceutical compositions containing them. The compounds and compositions are useful in the treatment of allergies.

15 Claims, No Drawings

2H-BENZOFURAN-3-ONE-DERIVATIVES AND PROCESS FOR THEIR PREPARATION

This is a continuation application of Ser. No. 002,380, filed Jan. 10, 1979, now abandoned.

The present invention relates to 2H-benzofuran-3-one derivatives, to a process for their preparation and to pharmaceutical compositions containing them.

The compounds of the invention have the following formula (I)

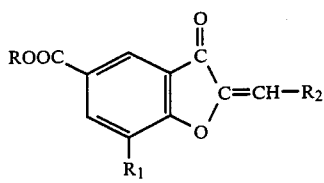

wherein

R is hydrogen or $C_1-C_{12}$ alkyl, unsubstituted or substituted by a

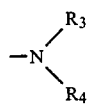

group, wherein each of $R_3$ and $R_4$ is independently selected from the group consisting of hydrogen and $C_1-C_6$ alkyl;

$R_1$ is hydrogen, $C_3-C_6$ alkenyl or $C_1-C_6$ alkyl;

$R_2$ is (a) thienyl or furyl, the thienyl and furyl groups being unsubstituted or substituted by a methyl group; or (b) the group

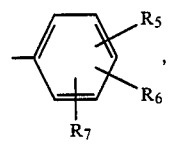

wherein each of $R_5$, $R_6$ and $R_7$ is independently selected from the group consisting of (a') hydrogen; (b') the group $-(O)_n-R_8$, wherein n is zero or 1 and $R_8$ is hydrogen or $C_3-C_4$ alkenyl or $C_1-C_6$ alkyl; and (c') the group

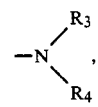

wherein $R_3$ and $R_4$ are as defined above.

Object of the present invention are also the pharmaceutically acceptable salts of the compounds of formula (I) as well as the possible isomers (e.g. optical antipodes and geometric isomers) and the mixtures thereof.

The numbering used to identify the position of the substituents in the $R_2$ radical is the conventional one as is shown by the following examples:

(a) when $R_2$ is phenyl;

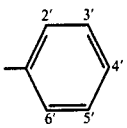

(b) when $R_2$ is furyl or thienyl:

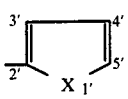

wherein X is oxygen or sulphur.

The alkyl, alkenyl and alkoxy groups may be branched or straight chain groups.

When R is an unsubstituted $C_1-C_2$ alkyl, it is preferably $C_1-C_6$ alkyl, in particular, methyl, ethyl, isopropyl, t.-butyl and hexyl.

When $R_1$ is $C_3-C_6$ alkenyl, it is preferably $C_3-C_4$ alkenyl.

When $R_1$ is $C_1-C_6$ alkyl, it is preferably $C_1-C_4$ alkyl.

When $R_3$ and/or $R_4$ are $C_1-C_6$ alkyl, the alkyl group is preferably $C_1-C_4$ alkyl, in particular, methyl, ethyl, isopropyl and t.butyl.

When $R_2$ is furyl or thienyl, it is preferably 2-furyl or 2-thienyl.

When $R_8$ is $C_1-C_6$alkyl, it is preferably methyl, ethyl, propyl or isopropyl.

When $R_8$ is $C_3-C_4$alkenyl, it is preferably allyl.

Preferably $R_5$, $R_6$ and $R_7$ are independently selected from the group consisting of hydrogen, $C_1-C_4$ alkoxy, in particular methoxy or ethoxy, and $C_1-C_4$ alkyl, in particular methyl and ethyl.

Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine di-(2-ethylhexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. critic, tartaric, maleic, malic, fumaric, methanesulphonic and ethanesulphonic acids.

Preferred salts are the sodium and the potassium salts, as well as the hydrochlorides of the basic esters, e.g. the diethylaminoethyl and dimethylaminoethyl esters.

Particularly preferred compounds of the invention are those of formula (I) wherein R is (a″) hydrogen or (b″) $C_1-C_6$ alkyl unsubstituted or substituted by

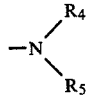

group, wherein each of $R_4$ and $R_5$, which are the same or different, is $C_1-C_4$ alkyl; $R_1$ is hydrogen or $C_1-C_4$ alkyl; $R_2$ is (a‴) phenyl unsubstituted or substituted by one to three substituents independently selected from the group consisting of $C_1-C_4$ alkyl, in particular methyl, and $C_1-C_4$ alkoxy, in particular methoxy or (b‴) 2-furyl, 2-thienyl, the furyl and the thienyl groups being unsubstituted or substituted by a methyl group, as well as their pharmaceutically acceptable salts.

In the most preferred compounds of the invention R is preferably hydrogen or a pharmaceutically acceptable cation.

Examples of particularly preferred compounds of the invention are:

5-carboxy-2-(2',5'-dimethoxy-benzylidene)-2H-benzofuran-3-one;
5-carboxy-2-(2'-ethoxy-5'-methoxy-benzylidene)-2H-benzofuran-3-one;
5-carboxy-2-(2'-propoxy-5'-methoxy-benzylidene)-2H-benzofuran-3-one;
5-carboxy-2-(2'-isopropoxy-5'-methoxy-benzylidene)-2H-benzofuran-3-one;
5-carboxy-2-(2'-allyloxy-5'-methoxy-benzylidene)-2H-benzofuran-3-one;
5-carboxy-2-(2',3',4'-trimethoxy-benzylidene)-2H-benzofuran-3-one;
5-carboxy-2-(3',4',5'-trimethoxy-benzylidene)-2H-benzofuran-3-one;
2-diethylaminoethyl ester of 5-carboxy-2-(2',3',4'-trimethoxy-benzylidene)-2H-benzofuran-3-one;
2-dimethylaminoethyl ester of 5-carboxy-2-(2',3',4'-trimethoxy-benzylidene)-2H-benzofuran-3-one, and the pharmaceutically acceptable salts thereof, in particular the sodium salts and the hydrochlorides of the basic esters (e.g. of those with 2-diethylaminoethanol and 2-dimethylaminoethanol) and the $C_1$–$C_6$ alkyl esters thereof, in particular the methyl, ethyl, isopropyl, t.-butyl and hexyl esters. The compounds of the invention are prepared by reacting a compound of formula (II)

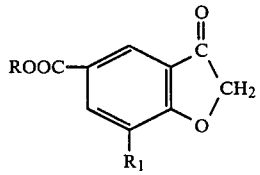
(II)

wherein R and $R_1$ are as defined above, with an aldehyde of formula (III)

 (III)

wherein $R_2$ is as defined above, and, if desired, converting a compound of formula (I) into another compound of formula (I) by known methods and/or, if desired, converting a compound of formula (I) into a pharmaceutically acceptable salt and/or, if desired, converting a salt into a free compound and/or, if desired, separating a mixture of isomers into the single isomers.

The reaction of a compound of formula (II) with an aldehyde of formula (III) may be preferably performed in an inert solvent such as, for example, a $C_1$–$C_4$ aliphatic alcohol, in particular methanol or ethanol, dioxane, benzene, toluene, xylene, tetrahydrofuran, water and their mixtures, in the presence of basic condensing agents such as, for example, sodium hydride, sodium amide, sodium methoxide, sodium ethoxide or in the presence of acid condensing agents such as, for example, sulphuric acid, hydrochloric acid, hydrobromic acid, phosphoric acid, p-toluenesulphonic acid at a temperature ranging from the room temperature to the reflux temperature.

Alternatively the reaction between a compound of formula (II) and an aldehyde of formula (III) may be performed by treatment with acetic anhydride at a temperature ranging from the room temperature to the flux temperature. A compound of formula (I) may be converted, as stated above, into another compound of formula (I) by known methods; for example, the compound of formula (I) wherein —COOR is an esterified carboxy group, may be converted into a compound of formula (I) wherein —COOR is carboxy by hydrolysis, e.g. basic hydrolysis, using, for example, sodium or potassium hydroxide, in a solvent, such as, e.g., water or a lower aliphatic alcohol, and operating at a temperature ranging from the room temperature to about 150° C.; the same reaction may be also carried out e.g. by treatment with lithium bromide in dimethylformamide at a temperature higher than 50° C.

A compound of formula (I) wherein —COOR is carboxy may be converted into a compound of formula (I) wherein —COOR is an esterified carboxy group, e.g. a carbalkoxy group unsubstituted or substituted by a

group, wherein $R_3$ and $R_4$ are as defined above, by conventional methods, for example by reacting the alkaline salt of the acid with the suitable alkyl halide, in an inert solvent, such as, e.g., acetone, dioxane, dimethylformamide, hexamethylphoshorotriamide at a temperature ranging from about 0° C. to about 100° C. Alternatively the esterification of a compound of formula (I) may be effected (a) converting the compound of formula (I) wherein —COOR is carboxy into the corresponding halocarbonyl, preferably chlorocarbonyl, derivative, by reaction, e.g., with the desired acid halide, for example oxalyl chloride, thionyl chloride, $PCl_3$, $PCl_5$ or $POCl_3$, either in the absence of solvents or in an inert organic solvent such as, e.g., benzene, toluene, xylene, dioxane, dichloroethane, methylene chloride, tetrahydrofurane, at a temperature ranging preferably from about 0° C. to about 120° C.; and then (b) reacting the obtained halocarbonyl derivative with the suitable alcohol of formula R—OH, wherein R is as defined above, in an inert solvent such as, e.g., benzene, toluene, xylene, dioxane, dichloroethane, methylene. chloride, tetrahydrofurane, at temperature varying between about 0° C. and about 120° C., preferably in the presence of a base, such as, e.g. triethylamine or diethylamine.

Also the optional salification of a compound of formula (I) as well as the conversion of a salt into the free compounds and the separation of a mixture of isomers into the single may be carried out by conventional methods. For example, the separation of optical antipodes into the single antipodes may be carried out by salification with an optically active base and by subsequent fractionated crystallization.

Thus, the separation of a mixture of geometric isomers may be carried out, for example, by fractionated crystallization.

The compounds of formula (II) may be prepared, for example, by treatment of a compound of formula (IV)

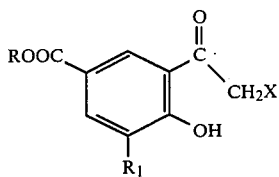

wherein R and $R_1$ are as defined above and X is Cl, Br, I, with a basis selected preferably from the group consisting of sodium and potassium carbonate, sodium and potassium bicarbonate, sodium and potassium acetate, pyridine, piperidine, triethylamine, in a solvent preferably selected from the group consisting, for example, of methanol, ethanol, acetone, dioxane, water and their mixtures at a temperature ranging between the room temperature and the reflux temperature.

The compounds of formula (IV) may be prepared, for example:

(a) by a Fries transposition of a phenyl ester of formula (V)

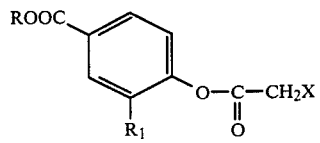

wherein R, $R_1$ and X are as defined above, performed by reacting a compound of formula (V) with $AlCl_3$ at a temperature ranging from the room temperature to about 170° C. in the presence of an inert solvent selected from the group consisting of, for example, nitrobenzene, dichloroethane, tetrachloroethane, or in the absence of a solvent;

(b) by reacting a compound of formula (VI)

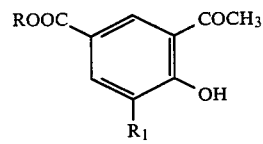

wherein R and $R_1$ are as defined above, with a halogenating agent selected from the group consisting of, for example, chlorine, bromine, bromodioxane, pyridine perbromide or, preferably, cupric bromide, in a solvent such as, for example, dioxane, dichloromethane, chloroform, dichloroethane, benzene, toluene, ethyl acetate and their mixtures at a temperature ranging from 0° C. to 100° C.

The compounds of formula (VI) may be prepared, for example, from suitable phenol derivatives by a Friedel-Crafts condensation or by a Fries transposition.

The compounds of the invention own anti-allergic activity, and are therefore useful in the prevention and treatment of all the affections of allergic origin, e.g. bronchial asthma, allergic rhinitis, hay fever, urticaria and dermatosis.

The anti-allergic activity of the compounds of the invention is shown, e.g., by the fact that they are active in the passive cutaneous anaphylaxis (PCA) test in rats, according to Goose J. and Blair A.M.J.N. (Immunology, 16, 749, 1969).

An important peculiarity of the compounds of the invention is that they exhibit high levels of anti-allergic activity also when orally administered.

The following table shows the activity values obtained in the PCA test in rats, after oral administration, for a number of compounds of this invention, identified by the codes: K 13422, K 13754, K 13383, K 13364, K 13432, in comparison with the well known anti-allergic drug Disodium Cromoglycate (DSCG).

Activity data are expressed in terms of $K_B$ defined as the dose of active compound capable of reducing to one half the activity of the serum used for the sensitization:

$$K_B = \frac{B}{DR - 1}$$

wherein
B=dose of antagonist compound expressed in mg/kg;
DR=dose ratio: antilogarithm of the distance between the Log dose effect functions of the serum with and without antagonist (J. H. Gaddum et al, Exp. Physiol., 1955, 40, 49).

The $K_B$ is adopted here because this value is independent both of the dose of the drug and the reagin concentration used for the sensitization. The lower the $K_B$ value, the higher the anti-allergic activity.

In the following table, the compounds of the invention are identified by the codes:
K  13422=5-carboxy-2-(2',3',4'-trimethoxy-benzylidene)-2H-benzofuran-3-one
K  13754=5-carboxy-2-(2'-ethoxy-5'-methoxy-benzylidene)-2H-benzofuran-3-one
K  13383=5-carboxy-2-(2',5'-dimethoxy-benzylidene)-2H-benzofuran-3-one
K  13364=5-carboxy-2-(3',4',5'-trimethoxy-benzylidene)-2H-benzofuran-3-one
K  13432=5-carboxy-2-(2'-isopropoxy-5'-methoxy-benzylidene)-2H-benzofuran-3-one

TABLE

| Compound | Pretreatment time | Anti-allergic activity $K_B$ (mg/kg) — p.o. |
|---|---|---|
| K 13422 | 15' | 1.87 |
| K 13754 | 15' | 2.55 |
| K 13432 | 15' | 3.56 |
| K 13383 | 15' | 3.71 |
| K 13364 | 15' | 5.94 |
| Disodium Cromoglycate | 15' | >200 |

The anti-allergic activity was determined by the inhibition of the IgE-mediated PCA according to Goose J. and Blair A.M.J.N. (loc.cit.) using homocytotropic antibodies raised in rats following the method of Mota I., Immunology, 7, 681, (1964).

The tested compounds were administered per os (p.o.) 15 minutes before the administration of the antigen: at least 6 rats were used for each dose. Seven days indicative acute toxicity after oral administration was assessed for the compounds of the invention, for example, a $LD_{50} > 800$ mg/kg in mice was obtained for all the following compounds of the invention:
5-carboxy-2-(2'-methoxy-benzylidene)-2H-benzofuran-3-one
5-carboxy-2-(3'-methoxy-benzylidene)-2H-benzofuran-3-one 5-carboxy-2-(4'-methoxy-benzylidene)-2H-benzofuran-3-one 5-carboxy-2-(2'-isopropoxy-benzylidene)-2H-benzofuran-3-one 5-carboxy-2-(3'-isopropoxy-benzylidene)-2H-benzofuran-3-one 5-carboxy-2-(3',4'-dimethoxy-benzylidene)-2H-benzofuran-3-one 5-carboxy-2-(2'-thenylidene)-2H-benzofuran-3-one 5-carboxy-2-(3',4',5'-trimethoxy-benzylidene)-2H-benzofuran-3-one 5-carboxy-2-(2'-5'-dimethoxy-benzylidene)-2H-benzofuran-3-one 5-carboxy-2-(2',3',4'-trimethoxy-benzylidene)-2H-benzofuran-3-one 5-carboxy-2-(2'-isopropoxy-5'-methoxy-benzylidene)-2H-benzofuran-3-one.

The compounds of the present invention furthermore possess anti-ulcer activity, as demonstrated by the fact that they proved to be active in inhibiting stress-induced ulcers in rats undergoing restraint in a water bath at 25° C. for 40 minutes according to a modification of the technique described by Takagi K and Okabe S. (Jap. J. of Pharmac., 1968, 19: 9).

The compounds of the invention own also bronchodilator activity, as shown by the fact that they proved to be active in inhibiting the bronchospasm induced by histamine in guinea-pigs according to the method of Kanzett and Rössler, Arch.Exp. Path.Pharmakol. 71, 195 (1940).

The compounds of the invention may be administered in conventional manner, for instance, orally and parenterally at a daily dosage preferably of 0.5 to 15 mg/kg, or by inhalation, preferably at a daily dosage of 0.5 to 100 mg, preferably 0.5 to 25 mg, or by topical application, e.g. by a cream containing about 0.5–5 mg, preferably 1–2 mg, of the active principle per 100 mg of cream.

The nature of the pharmaceutical compositions containing the compounds of this invention in association with pharmaceutically acceptable carriers or diluents will, of course, depend upon the desired mode of administration.

The compositions may be formulated in the conventional manner with the usual ingredients. For example, the compounds of the invention may be administered in the form of aqueous or oily solutions or suspensions, aerosols, as well as powders, tablets, pills, gelatine capsules, syrups, drops, suppositories, or creams, or lotions for topical use.

Thus, for oral administration, the pharmaceutical compositions containing the compounds of this invention, are preferably tablets, pills or gelatine capsules which contain the active substance together with diluents, such as, for example, lactose, dextrose, sucrose, mannitol, sorbitol, cellulose; lubricants, for instance, silica, talc, stearic acid, magnesium or calcium stearate, and/or polyethylene glycols; or they may also contain binders, such as, for example, starches, gelatine, methylcellulose, carboxymethylcellulose, gum-arabic, tragacanth, polyvinylpyrrolidone, disintegrating agents, such as, for instance, starches, alginic acid, alginates, sodium starch glycolate; effervescing mixtures; dyestuffs; sweeteners; wetting agents, such as, for instance, lecithin, polisorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

For the treatment of allergic asthma, the compounds of the invention are also administered by inhalation. For such use, suitable compositions may comprise a suspension or solution of the active ingredient, preferably in the form of a salt, such as the sodium salt, in water, for administration by means of a conventional nebulizer. Alternatively, the compositions may comprise a suspension or a solution of the active ingredient in a conventional liquified propellant, such as, dichlorodifluoromethane or dichlorotetrafluoroethane to be administered from a pressurized container, i.e., an aerosol dispenser. When the medicament is not soluble in the propellant, it may be necessary to add a co-solvent, such as, ethanol, dipropylene glycol, isopropyl myristate, and/or a surface-active agent to the composition, in order to suspend the medicament in the propellant medium and such surface-active agents may be any of those commonly used for this purpose, such as non-ionic surface-active agents, e.g., lecithin.

The compounds of the invention may also be administered in the form of powders by means of a suitable insufflator device and in this case the fine particle sized powders of the active ingredient may be mixed with a diluent material such a lactose.

Furthermore, the compounds of this invention may also be administered by intradermal or intravenous injection in the conventional manner.

In addition to the internal administration, the compounds of this invention may find use in compositions for topical application, e.g. as creams, lotions or pastes for use in dermatological treatments. For these compositions the active ingredient may be mixed with conventional oleaginous or emulsifying excipients.

The following examples illustrate but do not the present invention.

EXAMPLE 1

2'-hydroxy-5'-carbomethoxy-acetophenone (9.7 g) dissolved in 1:1 ethyl acetate-chloroform (100 ml) was reacted with cupric bromide (22.5 g) under stirring at reflux temperature for 20 hours.

After cooling and filtering, the organic solution was washed with 5% NaHCO$_3$ and water and then was evaporated to dryness in vacuo.

The residue was crystallized from ethanol so obtaining 2-bromo-2'-hydroxy-5'-carbomethoxy-acetophenone (8.5 g; m.p. 96°–98° C.); which was dissolved in methanol (100 ml) and treated with potassium acetate (11.76 g) at reflux temperature for five minutes.

After cooling, diluting with water and filtering, the residue was crystallized from methanol to give 5-carbomethoxy-2H-benzofuran-2-one (2.6 g; m.p. 102°–103° C.), which was dissolved in methanol (40 ml) containing 98% H$_2$SO$_4$ (0.3 ml) and reacted with benzaldehyde (1.6 g) at reflux temperature for 1 hour.

After cooling the precipitate was filtered and washed with water until neutral: 5-carbomethoxy-2-benzylidene-2H-benzofuran-3-one (2.1 g; m.p. 179°–180° C.) was obtained and reacted with 37% HCl (5 ml) in acetic acid (15 ml) at reflux temperature for 3 hours.

After cooling the precipitate was filtered and washed with ethanol and water to give 5-carboxy-2-benzylidene-2H-benzofuran-3-one, m.p.285°–287° C. (1.5 g). By proceeding analogously and starting from suitable substituted benzaldehyde, the following compounds were obtained:

5-carboxy-2-(2'-methyl-benzylidene)-2H-benzofuran-3-one, m.p. 265°–267° C.;
5-carboxy-2-(3'-methyl-benzylidene)-2H-benzofuran-3-one, m.p. 253°–254° C.;
5-carboxy-2-(4'-methyl-benzylidene)-2H-benzofuran-3-one, m.p. 228°–230° C.;
5-carboxy-2-(4'-isopropyl-benzylidene)-2H-benzofuran-3-one.

EXAMPLE 2

5-carbomethoxy-2-(3'-hydroxy-benzylidene)-2H-benzofuran-3-one, m.p. 214°–217° C. (20 mmoles) prepared according to Example 1 using 3'-hydroxy-benzaldehyde, was reacted with 2-bromo-propane (50 mmoles) in dimethylformamide (50 ml) in the presence of $K_2CO_3$ (50 mmoles) under stirring at 70° C. for 20 hours.

After dilution with ice water the precipitate was extracted with ethyl acetate: organic layer was evaporated to dryness to give a residue which was reacted with 1% KOH in 95% ethanol solution (25 mmoles) at reflux temperature for 10 minutes.

After cooling the reaction mixture was acidified with 23% HCl and the precipitate was filtered off and washed with ethanol and water: crystallization from ethanol gave 5-carboxy-2-(3'-isopropoxy-benzylidene)-2H-benzofuran-3-one, m.p. 277°–279° C.

By proceeding analogously and starting from suitable hydroxy-benzaldehydes, the following compounds were obtained:
5-carboxy-2-(2'-isopropoxy-benzylidene)-2H-benzofuran-3-one, m.p. 245°–246° C.;
5-carboxy-2-(4'-isopropoxy-benzylidene)-2H-benzofuran-3-one, m.p. 256°–258° C.;
5-carboxy-2-(2'-methoxy-benzylidene)-2H-benzofuran-3-one, m.p. 283°–284° C.;
5-carboxy-2-(3'-methoxy-benzylidene)-2H-benzofuran-3-one, m.p. 277°–279° C.;
5-carboxy-2-(4'-methoxy-benzylidene)-2H-benzofuran-3-one, m.p. 304°–306° C.

EXAMPLE 3

5-carbomethoxy-2-(2'-propoxy-benzylidene)-2H-benzofuran-3-one, m.p. 165°–167° C. (2.9 g) prepared according to Example 1 using 2-propoxy-benzaldehyde, was reacted with lithium bromide (11 g) in dimethylformamide (60 ml) at reflux temperature for 6 hours.

After cooling the reaction mixture was acidified with 23% HCl and diluted with water: the precipitate was filtered, washed with water until neutral, and crystallized from ethanol to give 5-carboxy-2-(2'-propoxy-benzylidene)-2H-benzofuran-3-one, m.p. 228°–229° C.

By proceeding analogously the following compounds were obtained:
5-carboxy-2-(2'-ethoxy-benzylidene)-2H-benzofuran-3-one, m.p. 272°–274° C.;
5-carboxy-2-(2'-butoxy-benzylidene)-2H-benzofuran-3-one, m.p. 225°–227° C.;
5-carboxy-2-(2'-allyloxy-benzylidene)-2H-benzofuran-3-one.

EXAMPLE 4

5-carbomethoxy-2H-benzofuran-3-one (3.1 g) dissolved in methanol (20 ml) containing 37% HCl (0.4 ml) was reacted with 2,3,4-trimethoxy-benzaldehyde (2.87 g) at reflux temperature for 1 hour.

After cooling the precipitate was filtered and washed with methanol and water until neutral to obtain 5-carbomethoxy-2-(2',3',4'-trimethoxy-benzylidene)-2H-benzofuran-3-one, m.p. 181°–183° C. (2.4 g), which was reacted with 1% KOH in 95% ethanol solution (46 ml) at reflux temperature for 10 minutes. After cooling the reaction mixture was acidified with 23% HCl and the precipitate was filtered off and washed with ethanol and water: further purification with hot ethyl acetate gave 5-carboxy-2-(2',3',4'-trimethoxybenzylidene)-2H-benzofuran-3-one, m.p. 247°–249° C. (1.3 g). By proceeding analogously, using the suitable disubstituted and trisubstituted benzaldehydes, the following compounds were obtained:
5-carboxy-2-(2',3'-dimethoxy-benzylidene)-2H-benzofuran-3-one, m.p. 265°–266° C.;
5-carboxy-2-(2',4'-dimethoxy-benzylidene)-2H-benzofuran-3-one, m.p. 312°–314° C.;
5-carboxy-2-(2',5'-dimethoxy-benzylidene)-2H-benzofuran-3-one, m.p. 264°–265° C.;
5-carboxy-2-(3',5'-dimethoxy-benzylidene)-2H-benzofuran-3-one, m.p. 300°–301° C.;
5-carboxy-2-(3',4'-dimethoxy-benzylidene)-2H-benzofuran-3-one, m.p. 257°–260° C.;
5-carboxy-2-(2'-ethoxy-3'-methoxy-benzylidene)-2H-benzofuran-3-one, m.p. 267°–269° C.;
5-carboxy-2-(2'-methoxy-3'-ethoxy-benzylidene)-2H-benzofuran-3-one, m.p. 243°–244° C.;
5-carboxy-2-(2'-isopropoxy-3'-methoxy-benzylidene)-2H-benzofuran-3-one, m.p. 262°–263° C.;
5-carboxy-2-(2'-ethoxy-5'-methoxy-benzylidene)-2H-benzofuran-3-one, m.p. 341°–343° C.;
5-carboxy-2-(2'-propoxy-5'-methoxy-benzylidene)-2H-benzofuran-3-one;
5-carboxy-2-(2'-allyloxy-5'-methoxy-benzylidene)-2H-benzofuran-3-one;
5-carboxy-2-(2'-isopropoxy-5'-methoxy-benzylidene)-2H-benzofuran-3-one, m.p. 254°–257° C.;
5-carboxy-2-(2',4',5'-trimethoxy-benzylidene)-2H-benzofuran-3-one, m.p. 288°–289° C.;
5-carboxy-2-(3',4',5'-trimethoxy-benzylidene)-2H-benzofuran-3-one, m.p. 292°–294° C.

EXAMPLE 5

By proceeding according to Example 4, starting from 5-carbomethoxy-7-propyl- and 5-carbomethoxy-7-allyl-2H-benzofuran-3-one, the following compounds were prepared:
5-carboxy-7-propyl-2-(2',5'-dimethoxy-benzylidene)-2H-benzofuran-3-one, m.p. 264°–266° C.;
5-carboxy-7-propyl-2-(2',3',4'-trimethoxy-benzylidene)-2H-benzofuran-3-one, m.p. 241°–242° C.;
5-carboxy-7-propyl-2-(3',4',5'-trimethoxy-benzylidene)-2H-benzofuran-3-one, m.p. 270°–272° C.;
5-carboxy-7-propyl-2-(2'-ethoxy-5'-methoxy-benzylidene)-2H-benzofuran-3-one;
5-carboxy-7-propyl-2-(2'-isopropoxy-5'-methoxy-benzylidene)-2H-benzofuran-3-one;
5-carboxy-7-allyl-2-(2',5'-dimethoxy-benzylidene)-2H-benzofuran-3-one;
5-carboxy-7-allyl-2-(2',3',4'-trimethoxy-benzylidene)-2H-benzofuran-3-one;

EXAMPLE 6

5-carbomethoxy-2H-benzofuran-3-one (14 g) dissolved in methanol (200 ml) saturated with gaseous HCl was reacted with 4-N,N-dimethylamino-benzaldehyde (18 g) at room temperature for 20 hours.

After evaporation to dryness the residue was reacted with 37% HCl (50 ml) in acetic acid (150 ml) at reflux temperature for 8 hours.

After cooling, dilution with water and neutralization with $K_2CO_3$, the precipitate was filtered off, washed with water and crystallized from dimethylformamide.

5-carboxy-2-(4'-N,N-dimethylamino-benzylidene)-2H-benzofuran-3-one (8.7 g).

By proceeding analogously the following compounds were prepared:

5-carboxy-2-(2'-N,N-dimethylamino-benzylidene)-2H-benzofuran-3-one.

EXAMPLE 7

5-carbomethoxy-2H-benzofuran-3-one (10 g) dissolved in methanol (100 ml) containing p-toluenesulphonic acid (1 g) was reacted with 2-thiophen-carboxaldehyde at reflux temperature for 2 hours.

After cooling the precipitate was filtered and washed with methanol and water so obtaining 5-carbomethoxy-2-(2-thenylidene)-2H-benzofuran-3-one, m.p. 185°–187° C. (8.9 g) which was reacted with lithium bromide (40 g) in dimethylformamide (200 ml) at 100° C. for 20 hours.

After cooling the reaction mixture was diluted with ice water and acidified with 37% HCl: the precipitate was filtered, washed with water until neutral and crystallized from ethanol to give 5-carboxy-2-(2-thenylidene)-2H-benzofuran-3-one, m.p. 310°–312° C. (5.3 g).

By proceeding analogously the following compounds were obtained:

5-carboxy-2-(5-methyl-2-thenylidene)-2H-benzofuran-3-one, m.p. 293°–295° C.;
5-carboxy-2-(3-methyl-2-thenylidene)-2H-benzofuran-3-one, m.p. 315°–317° C.;
5-carbomethoxy-2-(2-furfurylidene)-2H-benzofuran-3-one, m.p. 191°–193° C.;
5-carbomethoxy-2-(5-methyl-2-furfurylidene)-2H-benzofuran-3-one, m.p. 155°–157° C.;
5-carboxy-2-(2-furfurylidene)-2H-benzofuran-3-one;
5-carboxy-2-(5-methyl-2-furfurylidene)-2H-benzofuran-3-one.

EXAMPLE 8

5-carboxy-2-(2',3',4'-trimethoxy-benzylidene)-2H-benzofuran-3-one (7 g) was reacted with ethyl iodide (5.4 g) and anhydrous $K_2CO_3$ (6.3 g) in dimethylformamide (70 ml) under stirring at room temperature for 4 hours.

After dilution with water the precipitate was filtered and crystallized from 95% ethanol: 5-carbethoxy-2-(2',3',4'-trimethoxy-benzylidene)-2H-benzofuran-3-one (5.7 g) was obtained.

By proceeding analogously the following compounds were obtained:

5-carbethoxy-2-(2',5'-dimethoxy-benzylidene)-2H-benzofuran-3-one;
5-carbethoxy-2-(2'-ethoxy-5'-methoxy-benzylidene)-2H-benzofuran-3-one;
5-carbethoxy-2-(3',4',5'-trimethoxy-benzylidene)-2H-benzofuran-3-one;
5-carbethoxy-2-(2'-isopropoxy-5'-methoxy-benzylidene)-2H-benzofuran-3-one;
5-carbethoxy-2-(2'-propoxy-5'-methoxy-benzylidene)-2H-benzofuran-3-one;
5-carbethoxy-2-(2'-allyloxy-5'-methoxy-benzylidene)-2H-benzofuran-3-one.

EXAMPLE 9

By proceeding according to Example 7 the isopropyl, n-1-hexyl and n-1-undecyl esters of the following compounds were prepared:

5-carboxy-2-(2',5'-dimethoxy-benzylidene)-2H-benzofuran-3-one;
5-carboxy-2-(2'-ethoxy-5'-methoxy-benzylidene)-2H-benzofuran-3-one;
5-carboxy-2-(2',3',4'-trimethoxy-benzylidene)-2H-benzofuran-3-one;
5-carboxy-2-(3',4',5'-trimethoxy-benzylidene)-2H-benzofuran-3-one;
5-carboxy-2-(2'-isopropoxy-5'-methoxy-benzylidene)-2H-benzofuran-3-one;
5-carboxy-2-(2'-propoxy-5'-methoxy-benzylidene)-2H-benzofuran-3-one;
5-carboxy-2-(2'-allyloxy-5'-methoxy-benzylidene)-2H-benzofuran-3-one,

EXAMPLE 10

5-carboxy-2-(2',3',4'-trimethoxy-benzylidene)-2H-benzofuran-3-one (11 g) was reacted with thianyl chloride (6 ml) in dioxane (100 ml) at reflux temperature for 1 hour, then the mixture was evaporated to dryness in vacuo. The residue was dissolved in dioxane (80 ml) and triethylamine (2 ml) and was reacted with 2-diethylamino-ethanol (4 ml) at room temperature for 20 hours. After dilution with water the precipitate was filtered, dissolved in ethyl ether (100 ml) and treated with the stoichiometric amount of HCl in ether: the precipitate was filtered, washed in ethyl ether and dissolved in water. Alkalinization with $K_2CO_3$ and filtration of the precipitate gave 2-diethylaminoethyl ester of 5-carboxy-2-(2',3',4'-trimethoxy-benzylidene)-2H-benzofuran-3-one (7.1 g).

By proceeding analogously the following compounds were prepared:

2-diethylaminoethyl ester of 5-carboxy-2-(2',5'-dimethoxy-benzylidene)-2H-benzofuran-3-one;
2-diethylaminoethyl ester of 5-carboxy-2-(2'-ethoxy-5'-methoxy-benzylidene)-2H-benzofuran-3-one;
2-diethylaminoethyl ester of 5-carboxy-2-(3',4',5'-trimethoxy-benzylidene)-2H-benzofuran-3-one;
2-diethylaminoethyl ester of 5-carboxy-2-(2'-isopropoxy-5'-methoxy-benzylidene)-2H-benzofuran-3-one;
2-diethylaminoethyl ester of 5-carboxy-2-(2'-propoxy-5'-methoxy-benzylidene)-2H-benzofuran-3-one;
2-diethylaminoethyl ester of 5-carboxy-2-(2'-allyloxy-5'-methoxy-benzylidene)-2H-benzofuran-3-one.

EXAMPLE 11

By proceeding according to Example 9 the 2-dimethylaminoethyl esters of the following compounds were prepared:

5-carboxy-2-(2',5'-dimethoxy-benzylidene)-2H-benzofuran-3-one;
5-carboxy-2-(2'-ethoxy-5'-methoxy-benzylidene)-2H-benzofuran-3-one;
5-carboxy-2-(3',4',5'-trimethoxy-benzylidene)-2H-benzofuran-3-one;
5-carboxy-2-(2',3',4'-trimethoxy-benzylidene)-2H-benzofuran-3-one.

EXAMPLE 12

5-carboxy-2-(2',3',4'-trimethoxy-benzylidene)-2H-benzofuran-3-one suspended in benzene was reacted with the stoichiometric amount of 50% NaH at room temperature under stirring for 20 hours.

After filtration and washings with benzene and acetone the sodium salt of the 5-carboxy-2-(2′,3′,4′-trimethoxy-benzylidene)-2H-benzofuran-3-one was obtained.

By proceeding analogously the sodium salts of the following compounds were obtained:

5-carboxy-2-(2′,5′-dimethoxy-benzylidene)-2H-benzofuran-3-one;

5-carboxy-2-(2′-ethoxy-5′-methoxy-benzylidene)-2H-benzofuran-3-one;

5-carboxy-2-(3′,4′,5′-trimethoxy-benzylidene)-2H-benzofuran-3-one.

EXAMPLE 13

Tablets, each weighing 300 mg and containing 100 mg of the active substance are manufactured as follows:

Composition (for 10,000 tablets)

5-carboxy-2-(2′,3′,4′-trimethoxy-benzylidene)-2H-benzofuran-3-one: 1000 g
lactose: 1420 g
corn starch: 475 g
talc powder: 75 g
magnesium stearate: 30 g 5-carboxy-2-(2′,3′,4′-trimethoxy-benzylidene)-2H-benzofuran-3-one, lactose and half of the corn starch are mixed; the mixture is then forced through a sieve of 0.5 mm openings. Corn starch (35 g) is suspended in warm water (350 ml). The resulting paste is used to granulate the powder. The granules are dried, comminuted on a sieve of sieve size 1.4 mm, then the remaining quantity of starch, talc and magnesium stearate is added, carefully mixed, and processed into tablets using punches of 8 mm diameter.

EXAMPLE 14

Aerosol formulation 5-carboxy-2-(2′,3′,4′-trimethoxy-benzylidene)-2H-benzofuran-3-one: 2%
ethanol: 10%
lecithin: 0.2%
mixture of dichlorodifluoromethane and dichlorotetrafluoroethane (70:30 mixture): ad 100%.

We claim:

1. A compound of formula (I)

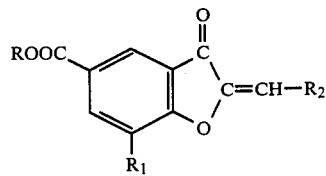

wherein

R is hydrogen or $C_1$–$C_2$ alkyl, unsubstituted or substituted by a

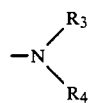

group, wherein each of $R_3$ and $R_4$ is independently selected from the group consisting of hydrogen and $C_1$–$C_6$ alkyl;

$R_1$ is hydrogen, $C_3$–$C_6$ alkenyl or $C_1$–$C_6$ alkyl;

$R_2$ is (a) thienyl or furyl, the thienyl and furyl groups being unsubstituted or substituted by a methyl group; or (b) the group

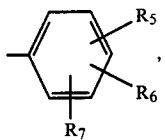

wherein each of $R_5$, $R_6$ and $R_7$ is independently selected from the group consisting of (a′) hydrogen; (b′) the group —(O)$_n$—$R_8$, wherein n is zero or 1 and $R_8$ is hydrogen or $C_3$–$C_4$ alkenyl or $C_1$–$C_6$ alkyl; and (c′) the group

wherein $R_3$ and $R_4$ are as defined above, as well as the pharmaceutically acceptable salts thereof.

2. A compound selected from the group consisting of:
5-carboxy-2-(2′,5′-dimethoxy-benzylidene)-2H-benzofuran-3-one;
5-carboxy-2-(2′-ethoxy-5′-methoxy-benzylidene)-2H-benzofuran-3-one;
5-carboxy-2-(2′-propoxy-5′-methoxy-benzylidene)-2H-benzofuran-3-one;
5-carboxy-2-(2′-isopropoxy-5′-methoxy-benzylidene)-2H-benzofuran-3-one;
5-carboxy-2-(2′-allyloxy-5′-methoxy-benzylidene)-2H-benzofuran-3-one;
5-carboxy-2-(2′,3′,4′-trimethoxy-benzylidene)-2H-benzofuran-3-one;
5-carboxy-2-(3′,4′,5′-trimethoxy-benzylidene)-2H-benzofuran-3-one;
2-diethylaminoethyl ester of 5-carboxy-2-(2′,3′,4′-trimethoxy-benzylidene)-2H-benzofuran-3-one;
2-dimethylaminoethyl ester of 5-carboxy-2-(2′,3′,4′-trimethoxy-benzylidene)-2H-benzofuran-3-one, and the pharmaceutically acceptable salts thereof.

3. A salt of a compound of claim 2, wherein the salt is the sodium salt.

4. A salt of a compound of claim 2, wherein the salt is the hydrochloride of a basic ester thereof.

5. A compound according to claim 4, wherein the basic ester is the 2-diethylaminoethanol or the 2-dimethylaminoethanol ester.

6. A $C_1$–$C_6$ alkyl ester of a compound of claim 2, wherein the $C_1$–$C_6$ alkyl group is methyl, ethyl, isopropyl, t-butyl or hexyl.

7. A process for the preparation of a compound of the formula (I)

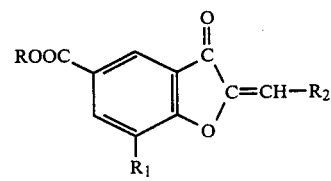

wherein

R is hydrogen or $C_1$-$C_{12}$ alkyl, unsubstituted or substituted by a

group, wherein each of $R_3$ and $R_4$ is independently selected from the group consisting of hydrogen and $C_1$-$C_6$ alkyl;

$R_1$ is hydrogen, $C_3$-$C_6$ alkenyl or $C_1$-$C_6$ alkyl;

$R_2$ is (a) thienyl or furyl, the thienyl and furyl groups being unsubstituted or substituted by a methyl group; or (b) the group

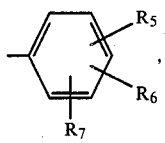

wherein each of $R_5$, $R_6$ and $R_7$ is independently selected from the group consisting of (a') hydrogen; (b') the group $-(O)_n-R_8$, wherein n is zero or 1 and $R_8$ is hydrogen or $C_3$-$C_4$ alkenyl or $C_1$-$C_6$ alkyl; and (c') the group

wherein $R_3$ and $R_4$ are as defined above, as well as the pharmaceutically acceptable salts thereof, said process comprising: reacting a compound of formula (II)

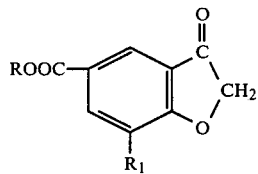

wherein R and $R_1$ are as defined above with an aldehyde of formula (III)

  (III)

wherein $R_2$ is as defined above.

8. A process according to claim 7, wherein a compound of formula (I) wherein —COOR is an esterified carboxy group is converted into a compound of formula (I) wherein —COOR is carboxy by hydrolysis.

9. A process according to claim 8 wherein said hydrolysis is carried out using sodium or potassium hydroxide in a suitable solvent.

10. A process according to claim 7, wherein a compound of formula (I) wherein —COOR is carboxy is converted into a compound of formula (I) wherein —COOR is an esterified carboxy group by reacting an alkaline salt of said carboxy group with a suitable esterifying agent.

11. A process according to claim 10, wherein said esterifying agent is a suitable alkyl halide.

12. A process according to claim 10, wherein said —COOR group in which R is hydrogen is converted into a corresponding halo carbonyl group using an acid halide, and then the resulting halo carbonyl derivative is reacted with an alcohol of formula ROH wherein R is as defined in claim 7.

13. A process according to claim 7, wherein a mixture of isomers of the compound of formula (I) is separated into single isomers by esterifying said mixture of isomers with an optically active base followed by fractionated crystallization.

14. A pharmaceutical composition comprising a compound according to claim 1 and a pharmaceutically acceptable carrier or diluent.

15. A method of treating allergies in a patient in need of such treatment, said method comprising administering to said patient a therapeutically effective amount of a compound according to claim 1.

* * * * *